(12) United States Patent
Shvabsky et al.

(10) Patent No.: US 7,824,905 B2
(45) Date of Patent: Nov. 2, 2010

(54) BIOLOGICAL REACTOR

(76) Inventors: Oleg Shvabsky, 2500 Parkview Dr. #2518, Hallandale Beach, FL (US) 33009; Jacob Gitman, 1111 Kane Concourse #518, Bay Harbor Island, FL (US) 33154

( * ) Notice: Subject to any disclaimer, the term of this patent is extended or adjusted under 35 U.S.C. 154(b) by 0 days.

(21) Appl. No.: 12/380,806

(22) Filed: Mar. 4, 2009

(65) Prior Publication Data

US 2010/0227389 A1    Sep. 9, 2010

(51) Int. Cl.
*C12M 1/00* (2006.01)
*C12M 3/00* (2006.01)

(52) U.S. Cl. ................................ 435/292.1; 47/1.4
(58) Field of Classification Search .............. 435/292.1; 47/1.4
See application file for complete search history.

(56) References Cited

U.S. PATENT DOCUMENTS

| 4,253,947 A * | 3/1981 | Fan et al. ................... 210/610 |
| 6,602,703 B2 * | 8/2003 | Dutil ....................... 435/292.1 |
| 2009/0178495 A1 * | 7/2009 | Steigmiller et al. ...... 73/863.72 |

* cited by examiner

*Primary Examiner*—William H Beisner
*Assistant Examiner*—Michael Hobbs
(74) *Attorney, Agent, or Firm*—I. Zborovsky

(57) ABSTRACT

A biological reactor for growing a biological mass has a tank with an interior for growing the biological mass, a plate movable in a substantially vertical direction and an interior of the tank, and a valve means provided with the plate and configured so that in a lower position of the plate the valve means are open, so that during displacement of the plate upwardly and downwardly, a solution in the interior of the tank is thoroughly fixed, while an upper position of the plate, the valve means are closed and the plate during movement downwardly provides a collection of a concentrated solution to be removed from the tank.

8 Claims, 5 Drawing Sheets

BIOLOGICAL REACTOR

BACKGROUND OF THE INVENTION

The present invention relates to biological reactors of a tank type for intense growing of a biological mass.

The biological reactors of this type are known in the art. In the known biological reactors, in order to separate the biological mass from an aqueous medium it is necessary to pore the whole solution outwardly for its subsequent separation, and then to put into the tank a fresh solution. This means additional vessels and energy consumption. It is also possible to move it to an upper position with a possibility of its natural filtration. During this process, growth of culture has to stop or takes place inefficiently.

Movements of a device for cleaning of a surface of inner light sources are performed by means of a screw-nut device. It is necessary to protect rubbing surfaces of these elements from adhesive products of the biosynthesis, which negatively affects the operation of the system.

SUMMARY OF THE INVENTION

Accordingly, it is an object of the present invention to provide a biological reactor of a tank, which avoids the disadvantages of the prior art.

In keeping with these objects and with others which will become apparent hereinafter, one feature of the present invention resides, briefly stated, in a biological reactor for growing a biological mass, comprising a tank with an interior for growing the biological mass; a plate movable in a substantially vertical direction in an interior of said tank, and a valve means provided with said plate and configured so that in a lower position of said plate said valve means are open, so that during displacement of said plate upwardly and downwardly, a solution in the interior of the tank is thoroughly fixed, while an upper position of said plate, said valve means are closed and said plate during movement downwardly provides a collection of a concentrated solution to be removed from said tank.

Another feature of the present invention resides, briefly stated, in a biological reactor stop means provided in an upper part of said tank and acting on said valve means for closing the latter.

Still another feature of the present invention resides, briefly stated, in a biological reactor wherein said valve means further comprises valve stems which in said lower position of said plate abut against a button of said tanks that valve means are opened.

A further feature of the present invention resides, briefly stated, in a biological reactor wherein a plurality of light sources extending substantially in a vertical direction through passages in said plate, said plate has cleaning means for cleaning said light sources during movement of said plate upwardly and downwardly.

Still an additional feature of the present invention resides, briefly stated, in a biological reactor wherein said plate is provided with filtering means for filtering of a water solution and collecting in a lower part of said tank a solution of a biological mass with a high concentration.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
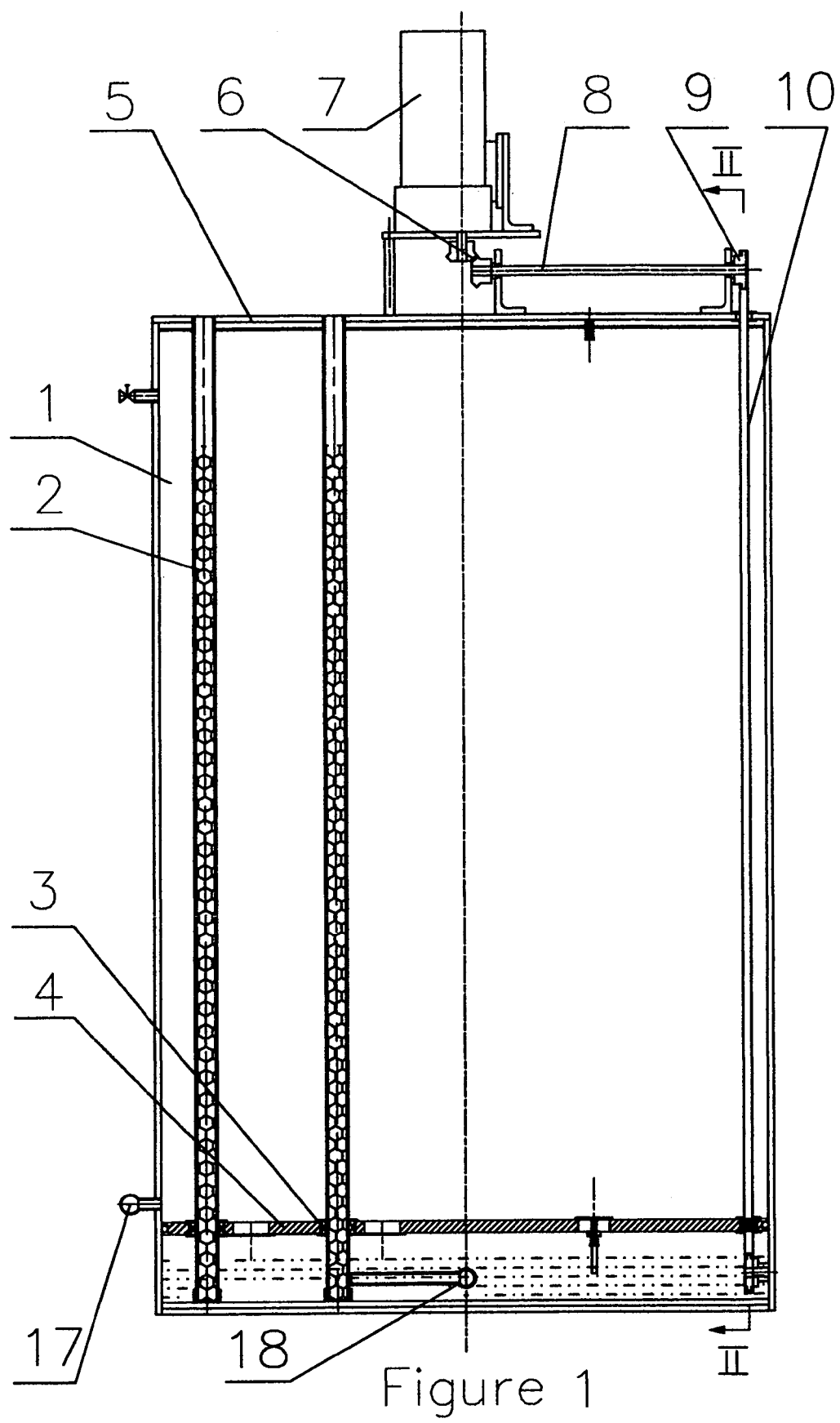
FIG. 1 is a view showing a growing of a cross-section of a biological reaction for growing a biological mass with plate located in its lower position.
Figure 2:
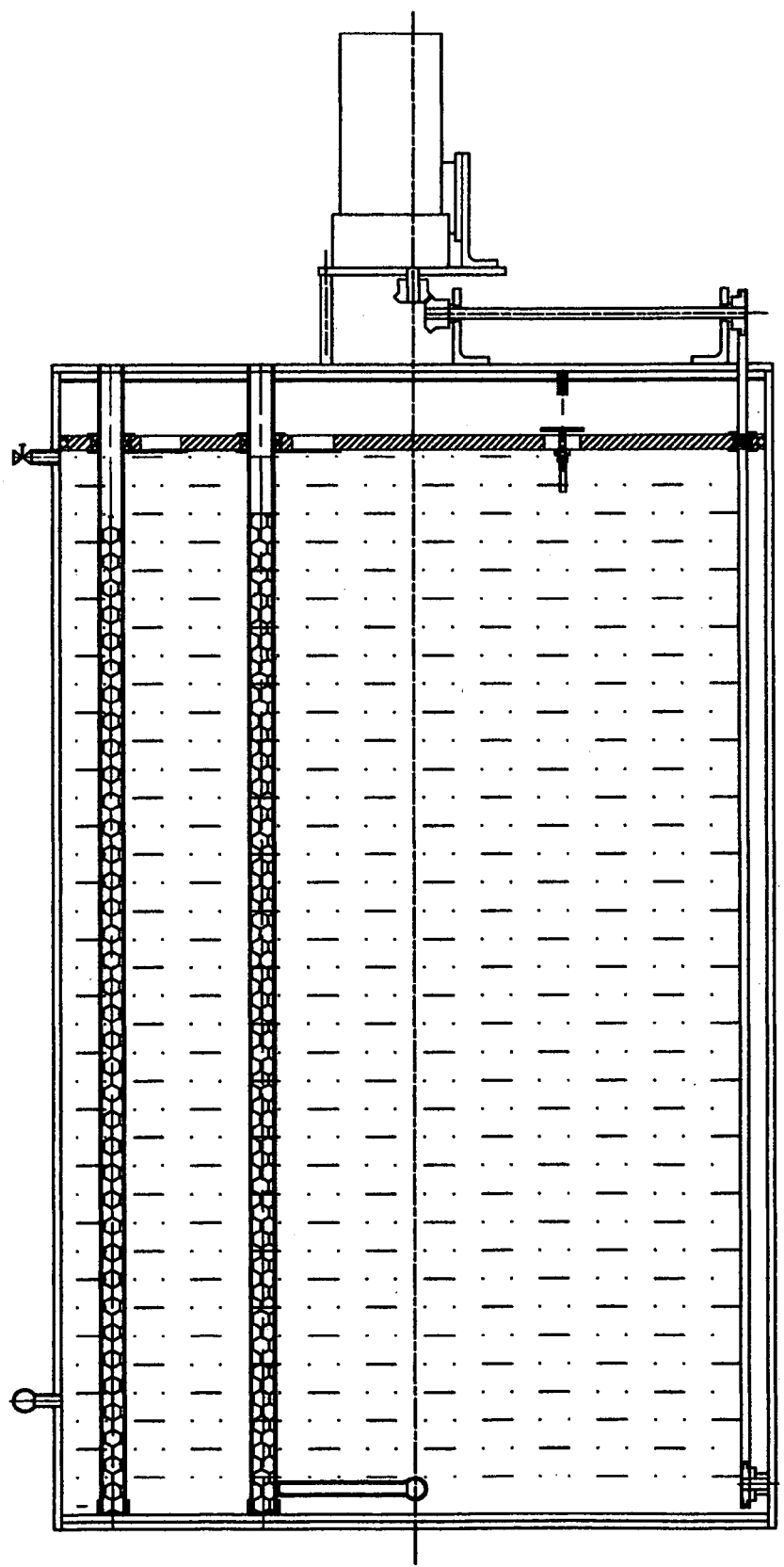
FIG. 2 is a view substantially corresponding to the view shown in FIG. 1, but with the plate located in its upper position.
Figure 3:
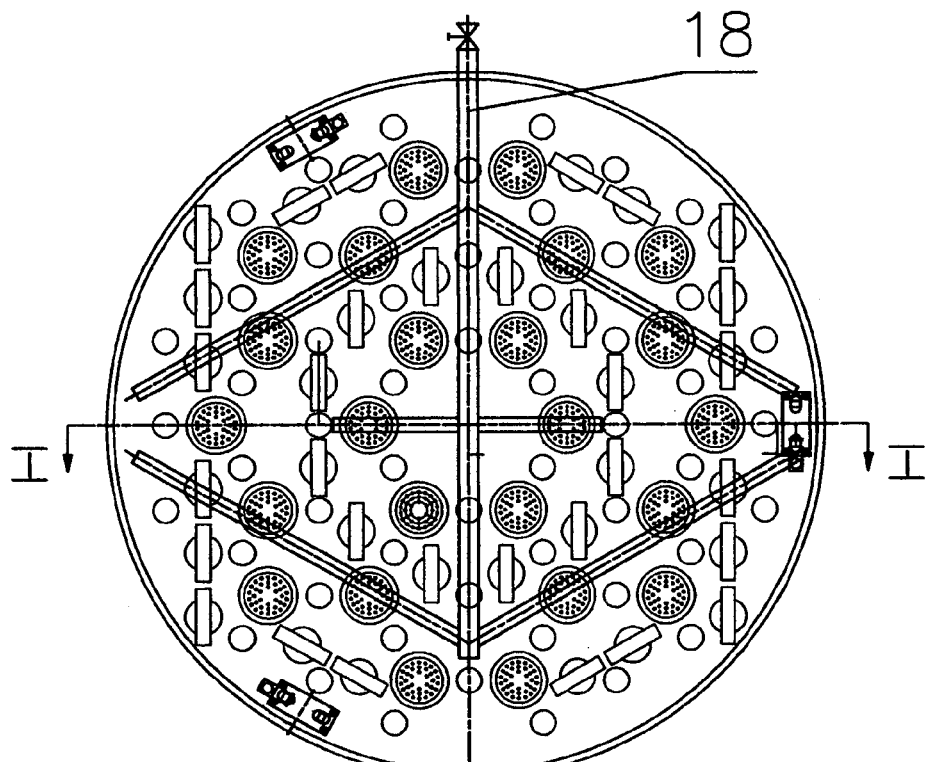
FIG. 3 is a plan view of the plate of the inventive biological reactor.
Figure 4:
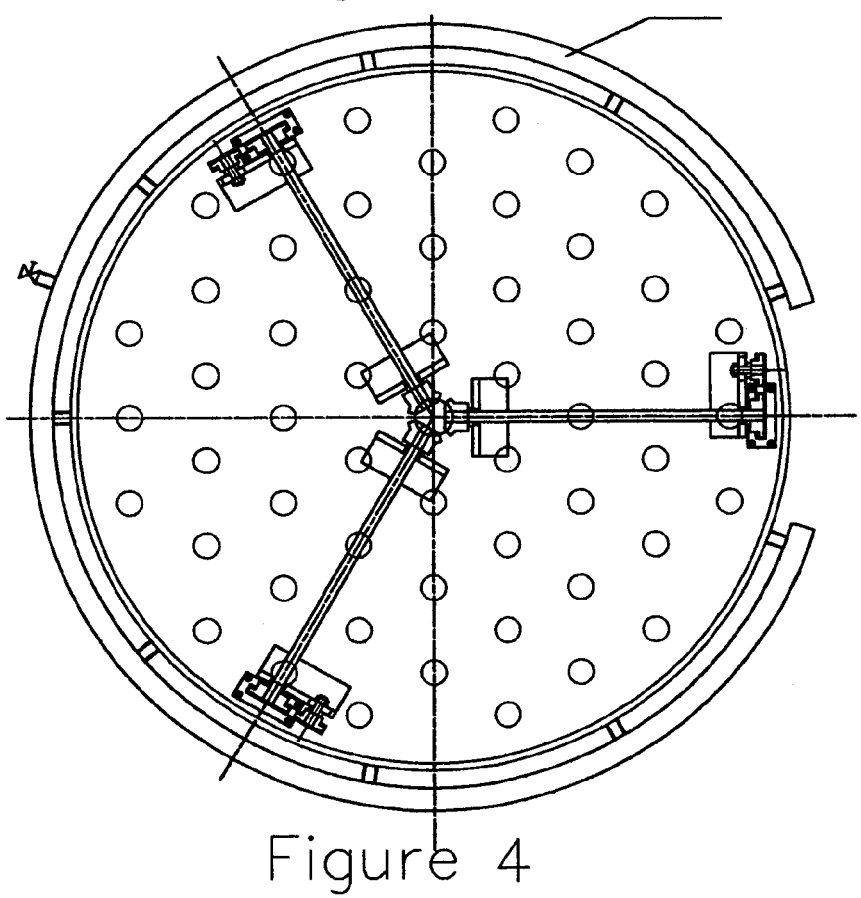
FIG. 4 is a view of an upper lid of the biological reactor in accordance with the present invention.
Figure 5:
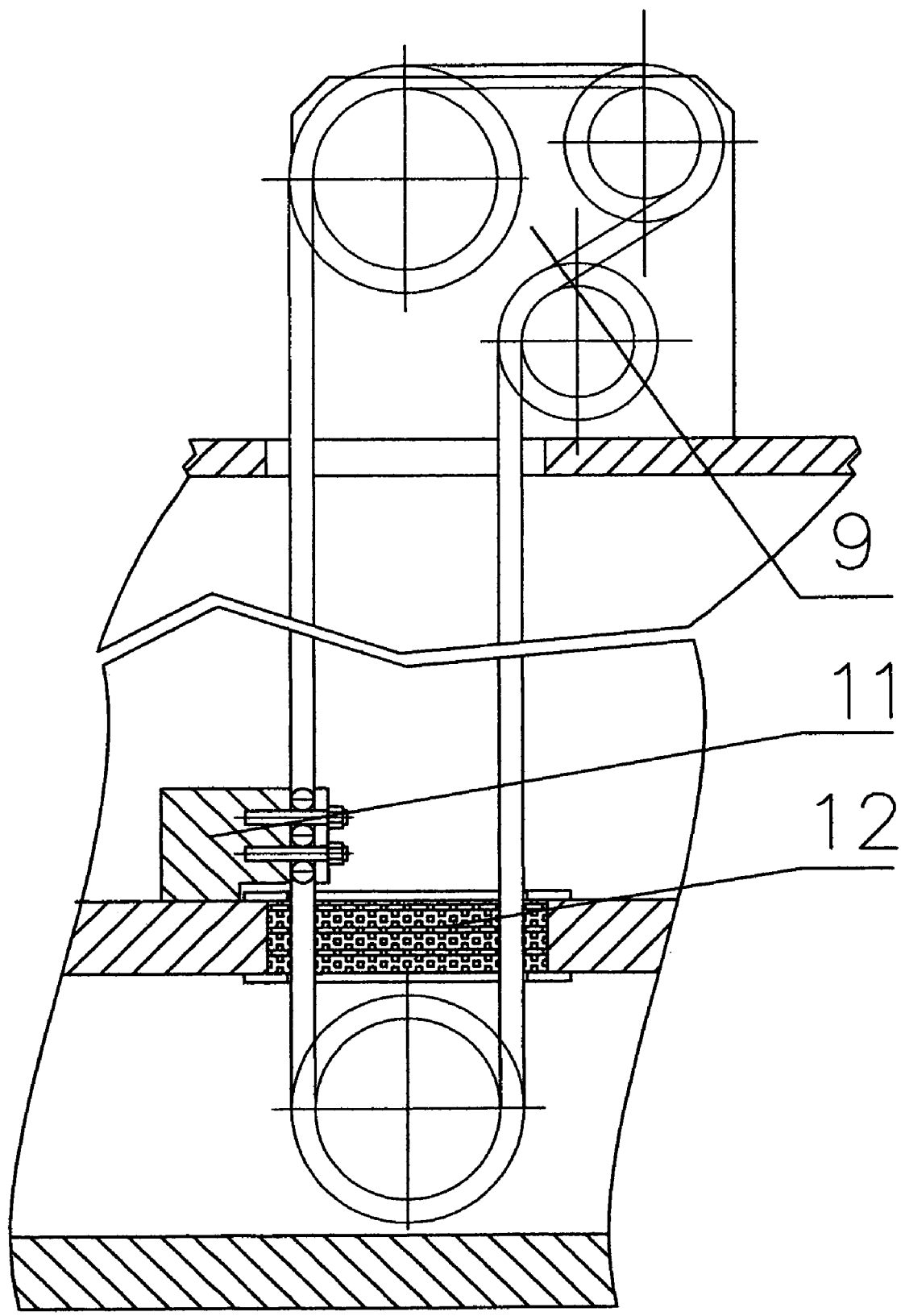
FIG. 5 is a view showing a cross-section of a chain unit of the inventive biological reactor.
Figure 7:
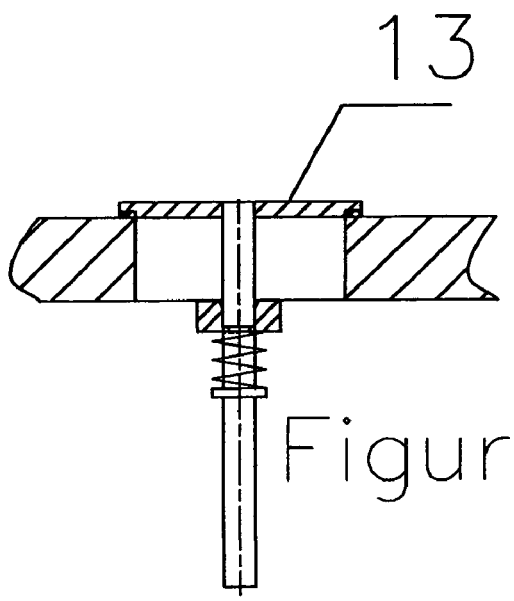
FIG. 7 is a view showing the valve of the biological reactor in a open position.
Figure 8:
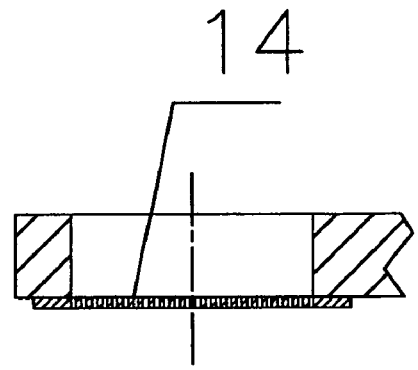
FIG. 8 is a view showing a cross-section of a filtering device.
Figure 6:
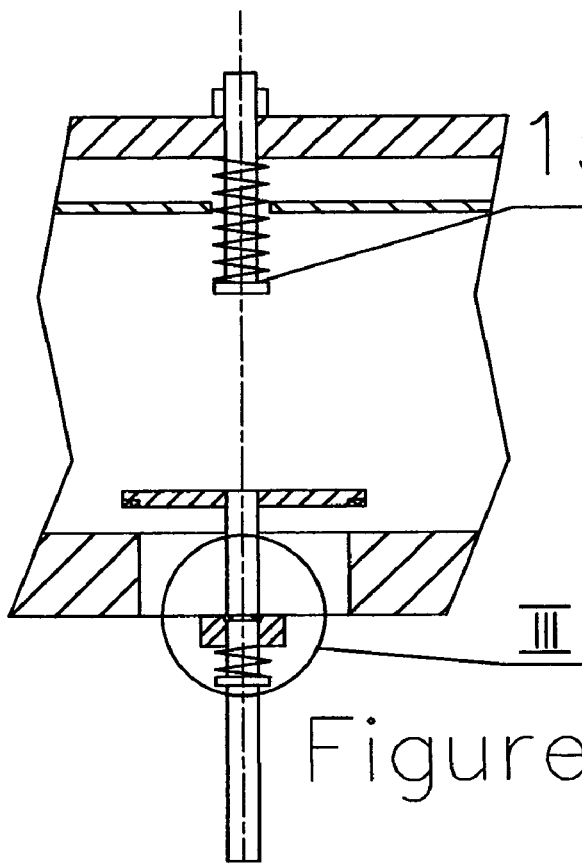
FIG. 6 is a view showing one of the valves of the inventive biological reactor in a closed position.
Figure 9:
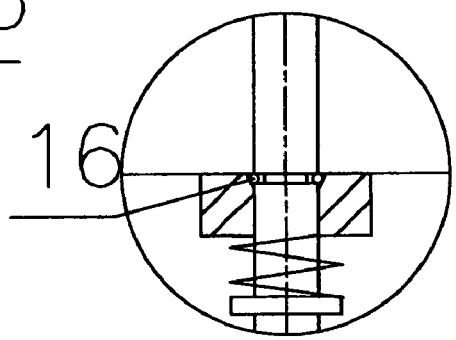
FIG. 9 is a view showing the filtering device on an enlarged scale.

A biological reactor of a tank type in accordance with the present invention has a tank which is identified with reference numeral 1. Light sources of the biological reactor are accommodated in glass pipes 2 in the interior of the tank 1.

Means for cleaning the pipes are identified with reference numeral 3 and can be formed as tubular cleaning elements.

The biological reactor in accordance with the present invention further has a movable plate which is identified with reference numeral 4. The tank 1 is closed from above by a lid 5. A conical tooth transmission 6 is driven from an electric motor 7 and includes shafts 8 and a chain block 9 formed for example as a roller chain sprocket. A roller chain is identified with reference numeral 10.

A device 11 provides fixing of the movable plate 4 to the chain 11.

The biological reactor further has a plurality of valves 13 which can each include a substantially vertical stem and a valve element and a substantially horizontal valve element operative for opening and closing of a corresponding through going aperture in the movable plate. A plurality of upper stops 15 are further provided in the tank 1. Springs 16 associated with corresponding grooves.

The biological reactor further has a collector for removing the biological mass 18 and a collector for supplying a fresh solution 17.

A seal 12 provides locking the area in order to avoid flowing of a solution between the upper and lower spaces of the tank During the operation of a device the plate 4 is moved up and down by electric motor 7 through the conical toothed transmission 6, three shafts of the chain block, to three points of conduct of the chain with the plate to provide a cant-free movement along the axis of the tank. The position of the plate is controlled by an electronic system of the biological reactor.

The biological reactor of a tank type in accordance with the present invention operates in the following manner.

When the plate is in its lower position and in contact with the bottom of the tank, the stems of the valves abut against the bottom of the tank and moved upwardly so as to open the apertures in the plate, and fixed in their upper position by the spring rings 16. During movements of the plate up and down the solution mixed thoroughly, the surface of the pipes of the light sources are cleaned.

When the plate moves in its upper position, the valve elements of the valves 13 are brought in contact with the stops 15, the spring rings 16 are displaced from the grooves, and the valves are closed. In this condition at the end of each cycle of growth of the biological mass, when the plate when the closed valve is moved down, the concentrated solution is collected and removed from the tank through the lower container, while a fresh portion of a solution of the required concentration is supplied through the upper container into the interior of the tank.

The filters 14 pass the cleaned water medium and allow passage of particles of flora for subsequent growth of the culture.

The cycle of operation of the reactor is carried out without starting of the process of growing of the biological mass.

It will be understood that each of the elements described above, or two or more together, may also find a useful application in other types of constructions differing from the type described above.

While the invention has been illustrated and described as embodied in a biological reactor, it is not intended to be limited to the details shown, since various modifications and structural changes may be made without departing in any way from the spirit of the present invention.

Without further analysis, the foregoing will so fully reveal the gist of the present invention that others can, be applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

The invention claimed is:

1. A biological reactor for growing a biological mass, comprising a tank with an interior for growing the biological mass; a plate movable in a substantially vertical direction and an interior of said tank, and a valve means acting with said plate wherein said valve means opens and closes a through-going aperture in the plate and configured so that in a lower position of said plate said valve means are open and during displacement of said plate upwardly a solution in the interior of the tank passes through said plate, while in an upper position of said plate, said valve means are closed and said plate during movement downwardly provides a collection of a concentrated solution to be removed from said tank.

2. A biological reactor as defined in claim 1, and further comprising stop means provided in an upper part of said tank and acting on said valve means for closing the latter, and wherein said valve means further comprises valve stems which in said lower position of said plate abut against a bottom of said tank so that said valve means are opened.

3. A biological reactor for growing a biological mass, comprising a tank with an interior for growing the biological mass; a plate movable in a substantially vertical direction and an interior of said tank, and a valve means acting with said plate wherein said valve means opens and closes a through-going aperture in the plate and configured so that in a lower position of said plate said valve means are open and during displacement of said plate upwardly a solution in the interior of the tank passes through said plate, while in an upper position of said plate, said valve means are closed and said plate during movement downwardly provides a collection of a concentrated solution to be removed from said tank, and a plurality of light sources extending substantially in a vertical direction through passages in said plate, said plate has cleaning means for cleaning said light sources during movement of said plate upwardly and downwardly.

4. A biological reactor as defined in claim 1, wherein said plate is provided with filtering means for filtering of a water solution and collecting in a lower part of said tank a solution of a biological mass with a high concentration.

5. A biological reactor as defined in claim 1, further comprising means for displacing said plate in a substantially vertical direction, including a motor, and transmission elements located inside said tank and connected with said plate for displacing said plate in a substantially vertical direction between said positions.

6. A biological reactor as defined in claim 1; and further comprising collector means associated with said tank for discharging said biological mass from said tank.

7. A biological reactor as defined in claim 1; and further comprising collector means associated with said tank for supplying a fresh solution into the interior of said tank.

8. A biological reactor as defined in claim 5, wherein said transmission elements include three said transmission elements extending transversely to said tank and connected with said plate in three points.

\* \* \* \* \*